(12) United States Patent
Mathews

(10) Patent No.: US 8,221,460 B2
(45) Date of Patent: Jul. 17, 2012

(54) METHODS AND DEVICES FOR INTERBODY SPINAL STABILIZATION

(75) Inventor: Hallett H. Mathews, Williamsburg, VA (US)

(73) Assignee: Warsaw Orthopedic, Inc, Warsaw, IN (US)

( * ) Notice: Subject to any disclaimer, the term of this patent is extended or adjusted under 35 U.S.C. 154(b) by 0 days.

(21) Appl. No.: 13/081,072

(22) Filed: Apr. 6, 2011

(65) Prior Publication Data

US 2011/0184422 A1     Jul. 28, 2011

Related U.S. Application Data

(60) Continuation of application No. 12/287,390, filed on Oct. 9, 2008, now abandoned, which is a continuation of application No. 11/363,122, filed on Feb. 27, 2006, now abandoned, which is a division of application No. 10/706,789, filed on Nov. 12, 2003, now abandoned, which is a division of application No. 09/918,332, filed on Jul. 30, 2001, now abandoned.

(51) Int. Cl.
*A61B 17/70* (2006.01)
*A61F 2/44* (2006.01)

(52) U.S. Cl. .................. 606/246; 606/90; 623/17.11

(58) Field of Classification Search .............. 623/17.11, 623/17.12; 606/90, 246
See application file for complete search history.

(56) References Cited

U.S. PATENT DOCUMENTS

| | | | |
|---|---|---|---|
| 4,969,888 | A | 11/1990 | Scholten et al. |
| 5,059,193 | A | 10/1991 | Kuslich |
| 5,108,404 | A | 4/1992 | Scholten et al. |
| 5,571,189 | A | 11/1996 | Kuslich |
| 5,827,289 | A | 10/1998 | Reiley et al. |
| 5,888,220 | A | 3/1999 | Felt et al. |
| 5,972,015 | A | 10/1999 | Scribner et al. |
| 6,102,928 | A | 8/2000 | Bonutti |
| 6,127,597 | A | 10/2000 | Beyar et al. |
| 6,171,299 | B1 | 1/2001 | Bonutti |
| 6,176,882 | B1 | 1/2001 | Biedermann et al. |
| 6,248,110 | B1 | 6/2001 | Reiley et al. |
| 6,632,235 | B2 | 10/2003 | Weikel et al. |
| 6,652,584 | B2 | 11/2003 | Michelson |
| 6,805,697 | B1 | 10/2004 | Helm et al. |
| 2001/0049527 | A1 | 12/2001 | Cragg |
| 2002/0026195 | A1 | 2/2002 | Layne et al. |
| 2002/0099384 | A1 | 7/2002 | Scribner et al. |
| 2003/0033017 | A1 | 2/2003 | Lotz et al. |

FOREIGN PATENT DOCUMENTS

| | | |
|---|---|---|
| WO | WO 98/56301 | 12/1998 |
| WO | WO 99/02214 | 1/1999 |
| WO | WO 99/08616 | 2/1999 |
| WO | WO 99/29246 | 6/1999 |
| WO | WO 99/59669 | 11/1999 |
| WO | WO 00/67650 | 11/2000 |

*Primary Examiner* — David H Willse
*Assistant Examiner* — Javier Blanco

(57) ABSTRACT

Methods and instruments for preparing a disc space and for forming interbody devices therein are provided. The instruments include distractors having enlargeable portions positionable in the disc space for distracting the disc space. The enlargeable portions can also provide form about or against which an interbody device of a first material is placed. A second material may be placed in the disc space in the space previously occupied by the distractors.

11 Claims, 11 Drawing Sheets

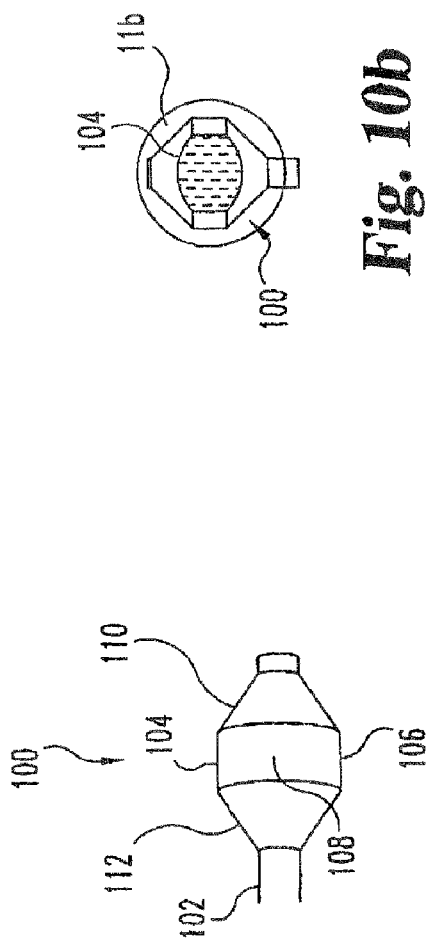
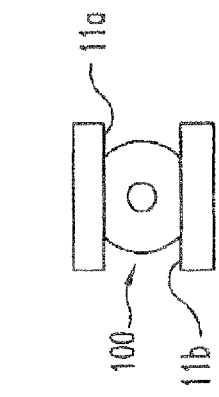
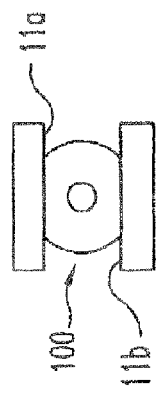
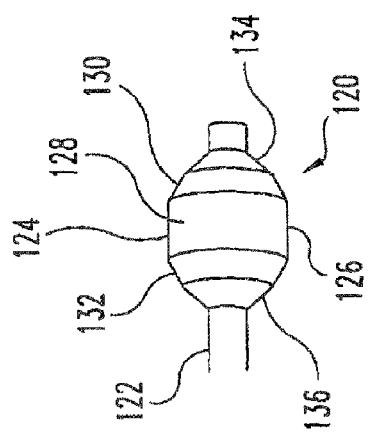

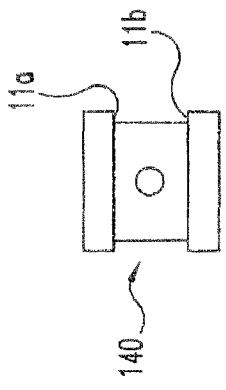
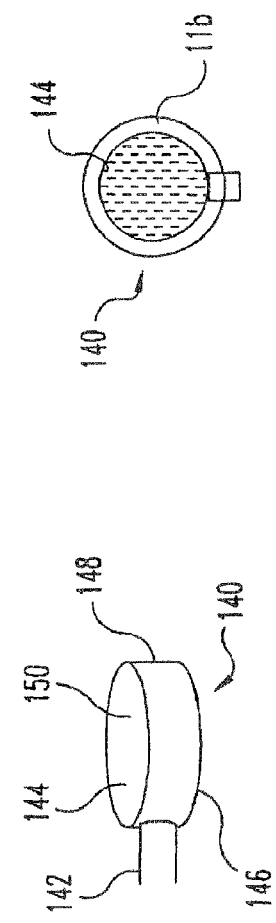
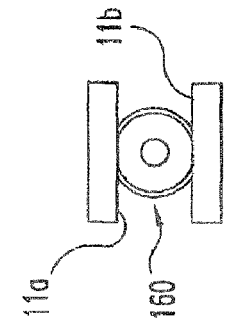
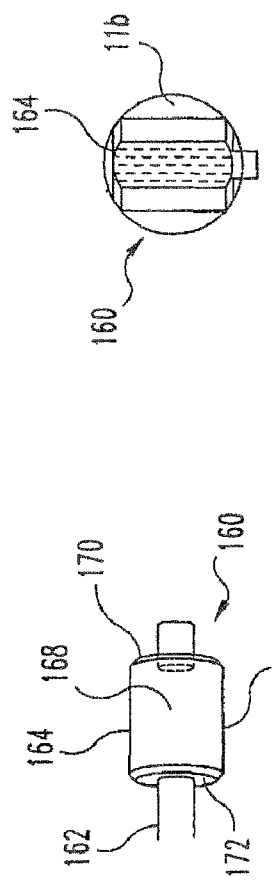

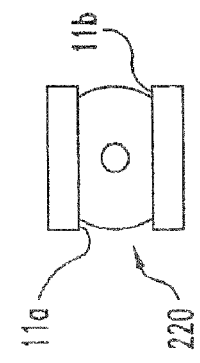
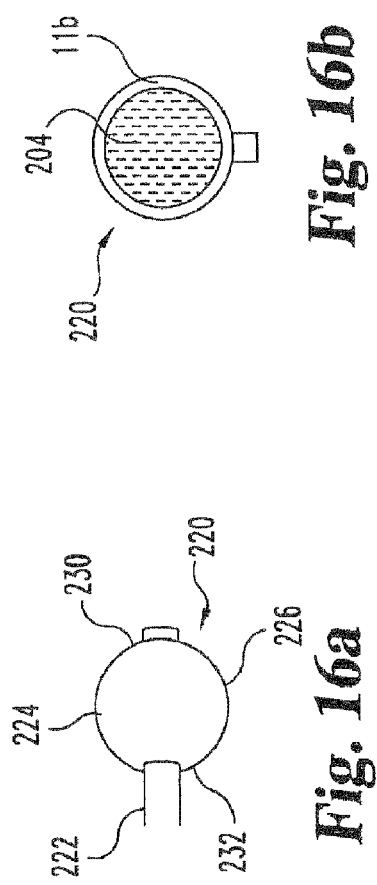
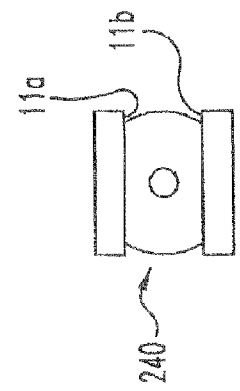
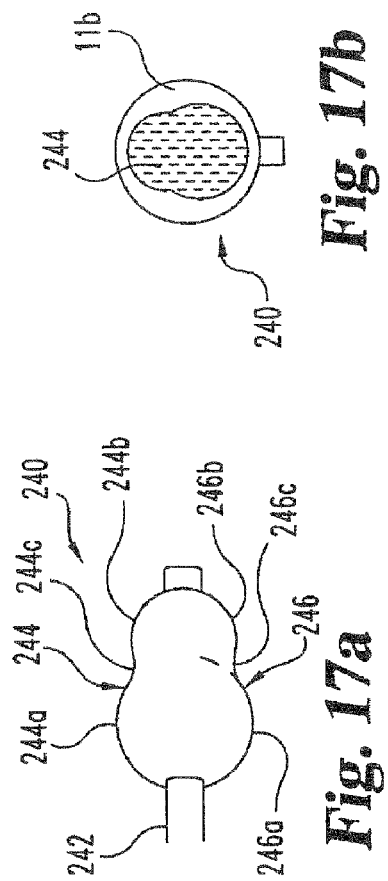

METHODS AND DEVICES FOR INTERBODY SPINAL STABILIZATION

CROSS-REFERENCE TO RELATED APPLICATIONS

This application is a continuation of U.S. patent application Ser. No. 12/287,390, filed Oct. 9, 2008 now abandoned, which is a continuation of U.S. patent application Ser. No. 11/363,122, filed Feb. 27, 2006 now abandoned, which is a divisional of U.S. patent application Ser. No. 10/706,789 filed on Nov. 12, 2003, now abandoned, which is a divisional of U.S. patent application Ser. No. 09/918,332, filed on Jul. 30, 2001, now abandoned, and each of the referenced applications is hereby incorporated by reference in its entirety.

FIELD OF THE INVENTION

The present invention relates generally to instruments and devices for spinal surgery, more particularly to methods and devices for spinal disc space preparation and interbody spinal stabilization.

BACKGROUND OF THE INVENTION

There are prior art interbody devices that are fabricated prior to implantation and then inserted into the patient's spinal disc space during surgery. It is also known to insert one or more pre-fabricated devices from anterior, antero-lateral, lateral, postero-lateral, transforaminal, posterior, posterior midline or any other known approach to the disc space. These pre-fabricated devices can require the surgeon to modify the interbody device, the vertebral bodies, and/or the vertebral endplates to achieve a desired fit between the spinal anatomy and the interbody device. While some pre-fabricated devices can be modified before and during surgery by the surgeon, this is a time consuming task and also does not always result in a desired or optimum fit with the natural or altered spinal anatomy. Further, the various approaches and instruments required to insert pre-fabricated devices can be invasive and traumatic to the nervature, vasculature, and tissue between the skin and the disc space.

What is therefore needed are methods and devices for providing interbody devices in a disc space between vertebral bodies that allow the surgeon to achieve a desired or optimum fit between the device and the natural or altered spinal anatomy. What is also needed are devices and methods for preparing a disc space for an interbody device while minimizing invasion into the tissue between the skin and the subject disc space. What is further needed are improved devices and methods for performing spinal surgery. What is also needed are methods and devices for providing interbody fusion utilizing minimally invasive approaches and instruments. The present invention is directed toward meeting these needs, among others.

SUMMARY OF THE INVENTION

According to one aspect of the present invention, there is provided a form positionable in a spinal disc space and an interbody device made from material that has a first condition allowing placement around the form and in contact with the vertebral endplates and thereafter the material has a second condition that provides structural support between the endplates.

According to another aspect of the invention, there is provided a distractor for a disc space that has a reduced-size configuration for insertion into a disc space and an enlarged configuration for distracting the disc space and for defining a void between the enlarged portion and the inner wall of the disc space annulus.

According to yet another aspect of the invention, a spinal disc space distractor provides an intradiscal form around which an interbody device is placed.

According to a further aspect of the invention, a spinal disc space distractor having an enlargeable portion is provided.

According to a further aspect of the invention, a spinal disc space distractor having an enlargeable portion with upper and lower vertebral endplate contact surfaces with predetermined areas is provided.

According to another aspect of the invention, a surgeon inserts a distractor in a spinal disc space and places a first material around the distractor and between the vertebral endplates. When the first material cures, the distractor is withdrawn and a second material is placed in the disc space in the space that was occupied by the distractor.

According to a further aspect of the invention, multiple distractors having enlargeable distracting portions are inserted in the disc space to form a void for receiving a first material.

According to another aspect of the invention, a disc space is hi-laterally distracted by inserting an enlargeable portion of a first distractor at a first lateral disc space location and an enlargeable portion of a second distractor at a second lateral disc space location. Scoliosis can be addressed by providing the enlargeable portions with different distraction heights.

According to a further aspect of the invention, a spinal disc space distractor having an enlargeable portion of a predetermined shape is provided. The predetermined shape is selected from one of the following: vertically-oriented cylinder, horizontally-oriented cylinder, sphere, cylindrical center portion with frusto-conical tapered ends; banana-shaped, and pear shaped.

These and other aspects, forms, features and advantages will be apparent from the following description of the illustrated embodiments.

BRIEF DESCRIPTION OF THE DRAWINGS

FIG. 2b is a diagrammatic illustration looking in the direction transverse to the sagittal plane of the spinal column segment encompassing the disc space and the distractor of FIG. 2a.

FIGS. 10*a*-10*c* show a side view, an end view and a plan view, respectively, of one embodiment of an inflatable distractor.

FIGS. 11*a*-11*c* show a side view, an end view and a plan view, respectively, of another embodiment inflatable distractor.

FIGS. 12*a*-12*c* show a side view, an end view and a plan view, respectively, of another embodiment inflatable distractor.

FIGS. 13*a*-13*c* show a side view, an end view and a plan view, respectively, of another embodiment inflatable distractor.

FIGS. 16*a*-16*c* show a side view, an end view and a plan view, respectively, of another embodiment inflatable distractor.

FIGS. 17*a*-17*c* show a side view, an end view and a plan view, respectively, of another embodiment inflatable distractor.

DESCRIPTION OF THE ILLUSTRATED EMBODIMENTS

Figure 1:
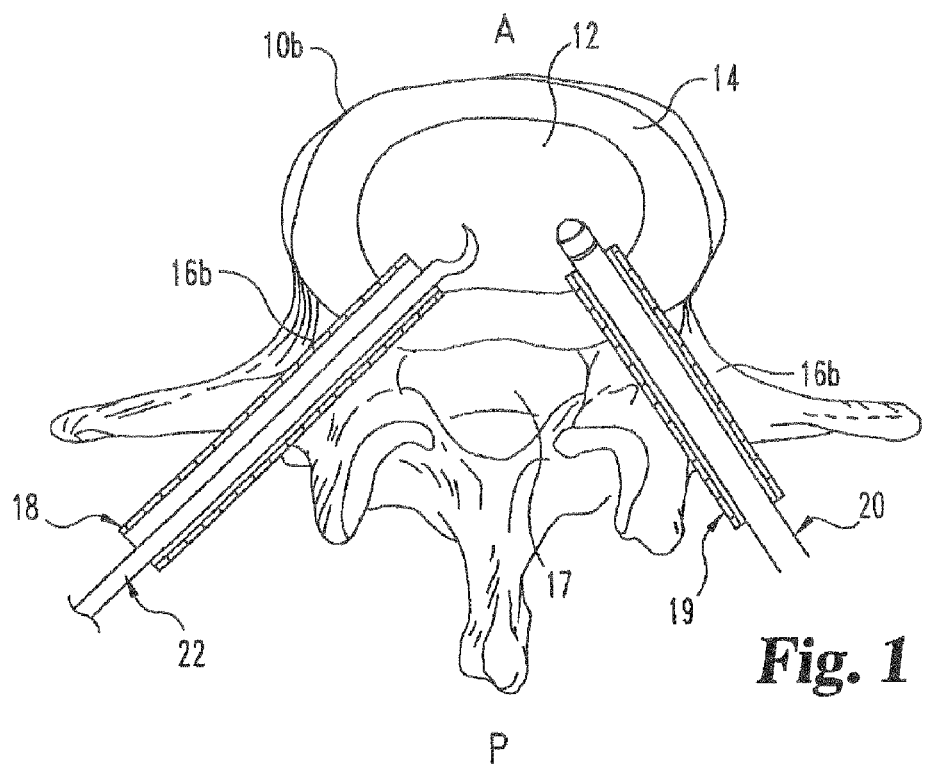
FIG. 1 is diagrammatic illustration in the axial plane of a spinal disc space with instruments positioned therein for performing a discectomy procedure.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and any such further applications of the principles of the invention as illustrated herein are contemplated as would normally occur to one skilled in the art to which the invention relates.

The present invention provides techniques for forming interbody devices in a disc space of the spinal column. It is contemplated that techniques of the present invention utilize minimally invasive endoscopic instruments and methods for performing discectomy and other disc space preparatory procedures. However, open surgical techniques and other visualization instruments and techniques are also contemplated. In techniques where the interbody device is part of a spinal fusion procedure, percutaneous stabilization and fixation techniques through the pedicles or facets are also possible after completing insertion of the interbody device. The present invention further provides minimally invasive techniques for segmental stabilization of a spinal disc space to repair a spinal disc space due to, for example, disc space collapse or progressive mono-segmental instability which are normally repaired via discectomy procedures that do not include interbody fusion. The present invention has application from any approach to any disc space along the spinal column, including L5-S1. Further, the present invention has application in a bi-portal, postero-lateral approach to one or disc spaces in the lumbar region of the spine.

Reference will now be made to FIGS. 1-7 to describe methods, instruments and materials according to the present invention to provide an interbody device formed in situ in the disc space that conforms with the patient's vertebral endplate anatomy. FIG. 1 shows an outline in plan view of a spinal disc space and lower vertebral body 10*b* in plan view during a discectomy procedure. The anterior aspect of the spinal column is indicated by "A" and the posterior side is indicated by "P." The lateral aspects of the spinal column extend between A and P on each side the spinal column. As shown further in FIG. 2*b*, the subject spinal disc space is located between an upper vertebra 10*a* having an inferior endplate 11*a* and a lower vertebral 10*b* having a superior endplate 11*b*. The disc space has a nucleus 12 that is surrounded by an annulus 14. First and second pedicles 16*a* extend posteriorly from upper vertebral body 10*a*, and first and second pedicles 16*b* extend posteriorly from lower vertebral body 10*b*. The spinal cord or dura 17 extends along the posterior aspect of vertebrae 10*a*, 10*b*.

In FIG. 1 there are shown instruments inserted via a bi-portal approach to the disc space that are useful in completing a nucleotomy or a discectomy of the spinal disc. The instruments for performing this procedure can include a scope 20 and a discectomy instrument 22. In the illustrated embodiment, discectomy instrument 22 and scope 20 are inserted through first access port 18 and second access port 19, respectively, in a postero-lateral approach to the disc space. Access ports 18, 19 can each be a working channel cannula to provide a protected first and second postero-lateral access ports to the disc space. It is to be understood that aspects of the present invention contemplate approaches and combinations of approaches to the disc space other than a postero-lateral approach, such as a lateral approach, anterior approach, or antero-lateral approaches. It should be understood that uni-portal disc space access is contemplated, as well as bi-portal disc space access from the same side of the spinal disc space or from differing approaches, such as a lateral approach and a postero-lateral approach. It is further contemplated that open surgical procedures could be utilized for the discectomy.

In one specific surgical technique used with the present invention, the disc space in the lumbar region of the spine is accessed endoscopically via a foraminal or postero-lateral, bi-portal approach. Cannulas and dilators can be used for access ports 18, 19 and catheters inserted therethrough for visualization, discectomy procedures, distraction, and material delivery. In these approaches, the outer cannulas can have an outside diameter of up to 7.5 millimeters and more typically in the range of about 6.5 millimeters. However, any sized cannula is contemplated so long as there is an acceptable level of trauma to the tissue and nerve structures.

To provide access ports 18, 19 in this specific technique, insertion begins 9 to 13 centimeters from the midline with a guidewire or discogram needle. The facet joint at the dome of the facet is initially targeted and palpated by the tip of the needle. The needle is withdrawn and re-angulated to go inside the dome, thus missing the exiting nerve root. The posterior vertebral bodyline is imaged fluoroscopically to document its resting position. The fluoro machine is then moved to an A-P position and the resting zone is either on the mid or lateral pendicular starting position for a postero-lateral approach or the medial pendicular midline for a foraminal approach. Needle insertion into the disc space can be completed simultaneously on the left and right hand sides. The needles can be triangulated to touch one another in the posterior central portion of the disc space or alignment can be adjusted and conformed via discography.

One or more dilators of increasing diameter are then sequentially placed over each of the needles to the annulus, and a cannula is placed over each of the final dilators to land on the annulus. The final dilators are removed and a trephine used through each cannula to cut holes in the annulus to allow for entry into the disc space. An endoscope can be used at any time throughout the procedure to document the presence of nerve roots or to observe the annulus prior to cutting. The final dilator is then re-inserted into each of the cannulas and impacted through the hole in the annulus and into the disc space. The final dilator thus secures the cannula into position and obstructs the annulus opening to ensure material is delivered into the disc space without excursion out of the disc space. The cannulas and dilators are then used as access portals to the disc space for completion of the remaining procedures, and also allow for the interchange of instruments between the left and right sides. Either one of the access ports 18, 19 can then be used for endoscopic visualization and the other access portal 18, 19 can be used for disc material removal with manual, automated, ultrasonic, laser, or any other disc material removal instruments desired by the surgeon.

After discectomy there is a prepared disc space 24. It can also be desired by the surgeon to expose and gently remove endplate cartilage and to remove all soft tissue and debris from within the disc space to expose the inner wall of the annulus. Inner portions of a minimally appropriate amount of the inner wall laminates of annulus 14 surrounding the removed nucleus can be removed to increase the lateral and anterior-posterior extent of the prepared disc space 24. The remaining portion of the annulus remains intact except for the access holes cut for instrument entry locations. An endoscope can be placed in one of the access portals to check disc material removal and to also check the annulus to ensure there are no wall defects requiring repair. In cases where interbody fusion is desired, the endplates can be prepared by eburnating the apophyseal ring to prepare it for bony fusion, and the vertebral endplates can be scraped or abraded to reduce them to bleeding bone. Right angle curettes or probes can also be inserted to make small protrusions or abrasions into the endplates to further facilitate fusion if so desired.

Figure 2A:
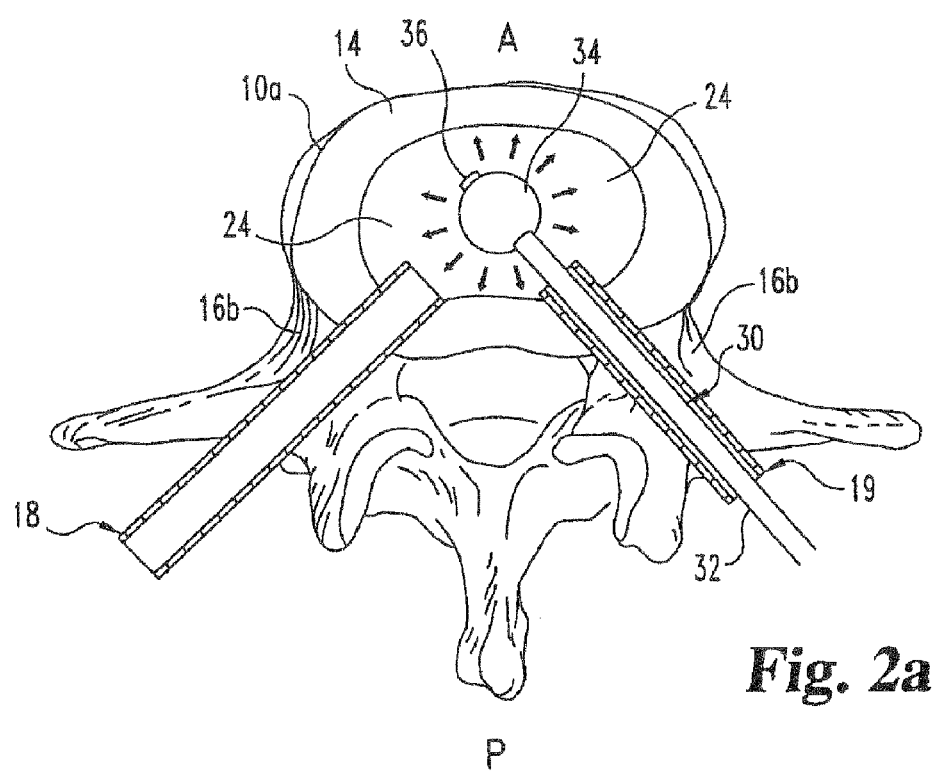
FIG. 2a is a diagrammatic illustration of the disc space of FIG. 1 with a distractor having an enlargeable portion positioned therein.
Figure 2B:
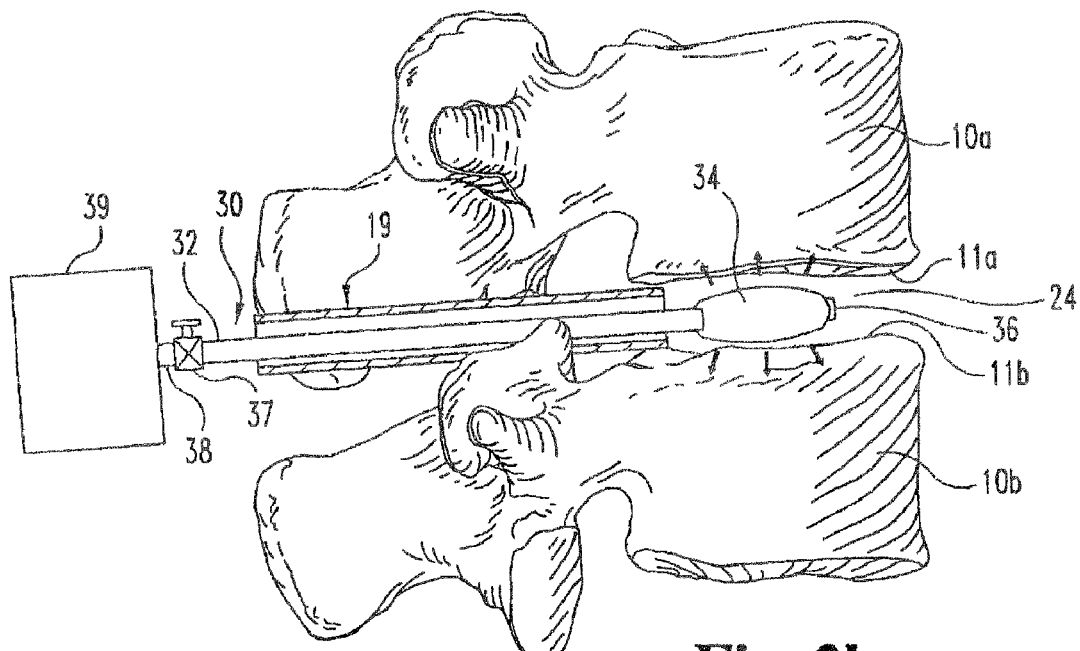

After disc space access and discectomy, the disc space will typically still be in a collapsed state, and the only distraction that has been completed at this point has been the result of insertion of the final dilator into the disc space. The disc space must now be further distracted to the desired disc space height and also to establish lordosis if desired or necessary. Referring now to FIGS. 2a-2b, a distractor 30 is inserted into the prepared disc space 24. Distractor 30 has a shaft 32 extending between a distal end 36 and a proximal end 38 situated outside the disc space. Adjacent distal end 36 there is an enlargeable portion 34 positionable in prepared disc space 24. Enlargeable portion 34 is inserted into the disc space in a reduced size configuration, and after proper positioning in prepared disc space 12 is confirmed endoscopically, fluoroscopically or via any other visualization technique, is thereafter enlarged to contact endplates 11a, 11b and distract the disc space to the desired height.

Figure 3A:
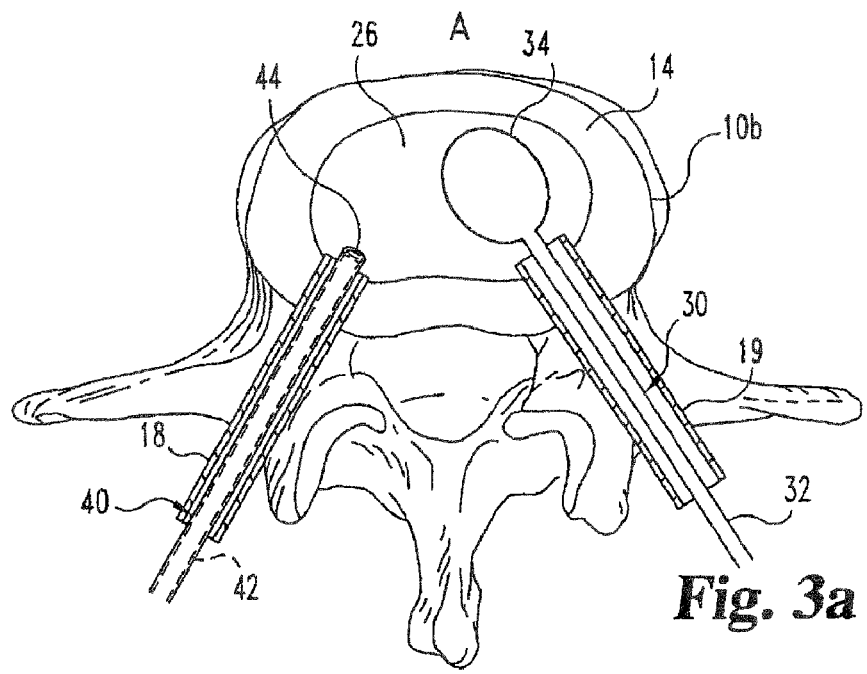
FIG. 3a is a diagrammatic illustration of the disc space of FIG. 2a with the distractor disposed therein along with a material delivery instrument.

Enlargeable portion 34 is sized with respect to prepared disc space 24 such that a void 26 is formed between the enlarged portion 34, inner wall of annulus 14, and the endplates 11a, 11b generally in the location of the apophyseal ring as shown in FIG. 3a. In one form, enlargeable portion 34 is an inflatable balloon or cuff-type structure that is inserted into the disc space in a deflated condition and thereafter inflated via an inflation lumen through shaft 32 to a predetermined pressure with air, gas, or liquid from an inflation source 39. A valve 37 can be provided on shaft 32 to block the lumen therethrough and maintain the inflation pressure in enlargeable portion 34. It is further contemplated that enlargeable portion 34 could be made from any material capable of assuming a reduced sized for insertion and withdrawal from the prepared disc space and enlargeable for disc space distraction, such as an elastomer, polymer, shape memory material or spring steel. Examples of various types of inflatable devices are described further below with respect to FIGS. 10-17.

In any event, enlargeable portion 34 is sized in the cephalad-caudal directions sufficiently to distract the spinal disc space to a desired normal disc space height and sized in the lateral and anterior-posterior directions to provide void 26 when enlarged. A single centrally placed enlargeable distractor 30 could utilize endplate geometry to create lordosis.

In addition to a single distractor having an enlargeable portion inserted into the disc space as shown above with respect to FIGS. 1-7, other distraction instruments and techniques are contemplated. For example, if the enlargeable portion of the distractor is inflatable, then the enlargeable portion 34 can be provided with dual chambers of differing heights to establish a lordotic effect. In another example, multiple distractors having different height enlargeable portions 34 can be inserted and positioned at the appropriate locations in the disc space and be enlarged together to provide the desired endplate angulation.

Figure 3B:
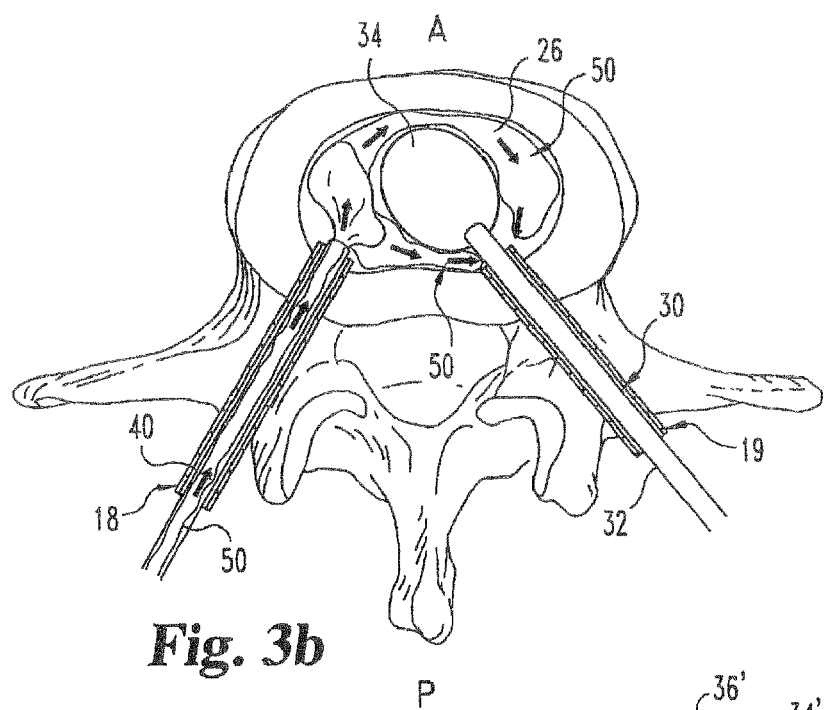
FIG. 3b is a diagrammatic illustration of the disc space of FIG. 3a with a first material being delivered around the enlarged portion of the distractor.
Figure 4:
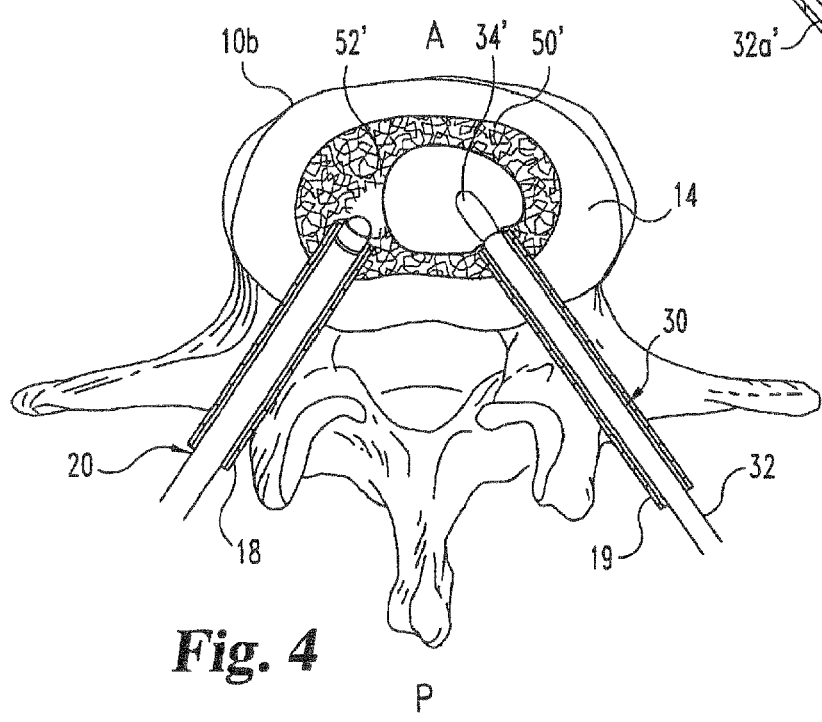
FIG. 4 is a diagrammatic illustration of the disc space of FIG. 3b after the first material has cured and the enlargeable portion of the distractor in a reduced size configuration for removal from the disc space.

As further shown in FIGS. 3a and 3b, with distractor 30 enlarged and maintaining disc space distraction, a material delivery instrument 40 is inserted into the disc space in the access port opposite the distractor access port. Material delivery instrument 40 includes a working channel 42 through which a first material 50 can be delivered through a distal opening 44 and into void 26. First material 50 has a first condition that allows it to be selectively placed, injected, flowed, moved or otherwise migrated around the enlargeable portion 34 in void 26 such that all or substantially all of void 26 is occupied by first material 50. First material 50 thereafter changes, cures or transforms from its first condition into a second condition in which it forms a solid or semi-solid interbody device 50' in space 26, as shown in FIG. 4, capable of structurally supporting the vertebrae at the desired disc space height. Interbody device 50' thus conforms to the patient's vertebral endplate anatomy and also conforms to the shape of void 26 between enlargeable portion 34 and annulus 14.

It is contemplated that first material 50 can be a cement, poly(methyl methacrylate), or any other bio-compatible material that has the structural capabilities to withstand the spinal column loads applied thereto. It is further contemplated that first material 50 can be delivered in a first condition through an instrument channel or lumen of instrument 40 and thereafter changed to a second condition via any natural or chemically induced or enhanced reaction to form an interbody device 50'. First material 50 can further be static or include bio-active material to promote bone growth.

Figure 3C:
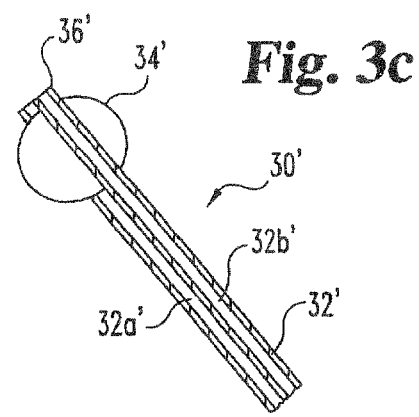
FIG. 3c is a sectional view of an alternate embodiment enlargeable distractor and material delivery instrument according to the present invention.

While delivery instrument 40 is illustrated as an instrument separate from distractor 30, it is also contemplated that distractor 30 could be provided with a working channel for delivery of first material 50 to void 26 or second material 60 to central space 52'. For example, as shown in FIG. 3c, distractor 30' has a shaft 32' and an inflatable enlargeable portion 34'. Shaft 32' defines an inflation lumen 32a' in communication with the interior of enlargeable portion 34'. Shaft 32' further include a material delivery lumen 32b' extending through enlargeable portion 34' and opening at distal end 36'. After distraction with enlargeable portion 34', first material 50 can be delivered through lumen 32b' into void 26. Such an instrument could be employed for uni-portal material delivery and disc space distraction, or used in combination with material delivery instrument 40 or another distractor 30' in the opposite access port to provide bi-portal material delivery. It is further contemplated that delivery instrument 40 can be a flexible cannula or catheter that can be moved or manipulated around void 26 in order to deliver first material 50 to all portions thereof. Material delivery instrument 40 can further be provided with endoscopic capabilities to allow visualization and direct viewing of material delivery.

In another form, one or more flexible material delivery catheters can be placed over a guide wire extending through one of the access portals and into the disc space around enlargeable portion 34 and at various locations in void 26. The flexible catheter(s) can be placed through only one or both of the access portals 18, 19. With the desired distraction achieved and the material delivery catheters positioned as desired, the guide wires are removed and first material 50 delivered through the flexible catheter(s). First material 50 can be delivered sequentially through the catheters or simultaneously through the catheters to provide an interbody device 50' that is completely formed about enlargeable portion 34 except for an entry port to central cavity 52'. Interbody device 50' thus provides balanced spinal load support on the apophyseal ring. Second material 60 can then be placed centrally into the interbody device in the central cavity 52' previously occupied by the withdrawn enlargeable portion 34 of distractor 30.

One specific technique for placement of first material 50 via bi-portal, postero-lateral access ports was completed as follows. The material delivery instrument 40 included first and second material delivery catheters each placed in a respective one of the first and second access ports 18 and 19. First material 50 was delivered through one catheter through the first access port under low pressure until the presence of first material 50 was detected at the distal end of the first access port or the second access port. The catheter was then slowly pulled back through the first access port until first material 50 was delivered to the distal end of the first access port housing the first delivery catheter. Thereafter the first material delivery catheter was withdrawn. First material 50 was then delivered through the second material delivery catheter positioned in the second access port until first material 50 was detected at the distal end of either of the second access port or the first access port. The second material delivery catheter was then pulled back through the second access port, thereby completely filling the void 26 with first material 50.

Several factors are to be considered in placing first material 50 in the disc space. For example, if first material 50 were a cement, factors to consider include the liquidity of the cement, the cure temperature of the cement and the insertion pressure of the cement. If the cement has a relatively cool temperature, then more time is required for the cement to cure which increase operating room time. Curing time can also be affected by adding other substances to it, such as growth factors, antibiotics and/or barium tracer. The injection pressure of first material 50 can affect whether it will leak out of small tears in the annulus or infiltrate interstices and nutrient canals of the vertebral endplates. It is also desirable that placement procedures for first material be carried out under fluoroscopy with a tracer such as barium in first material 50 to allow monitoring of material excursion and its presence in the disc space. Monitoring of the placement of first material 50 to confirm its proper positioning in the disc space can be accomplished by AP and lateral fluoroscopy or bi-planar fluoroscopy. The presence of material excursion could signify a significant annulus or other anatomical or surgically created defect or void. Such monitoring provides a safety measure to ensure first material 50 is not placed into inappropriate anatomic locations during formation of interbody device 50'.

Figure 5:
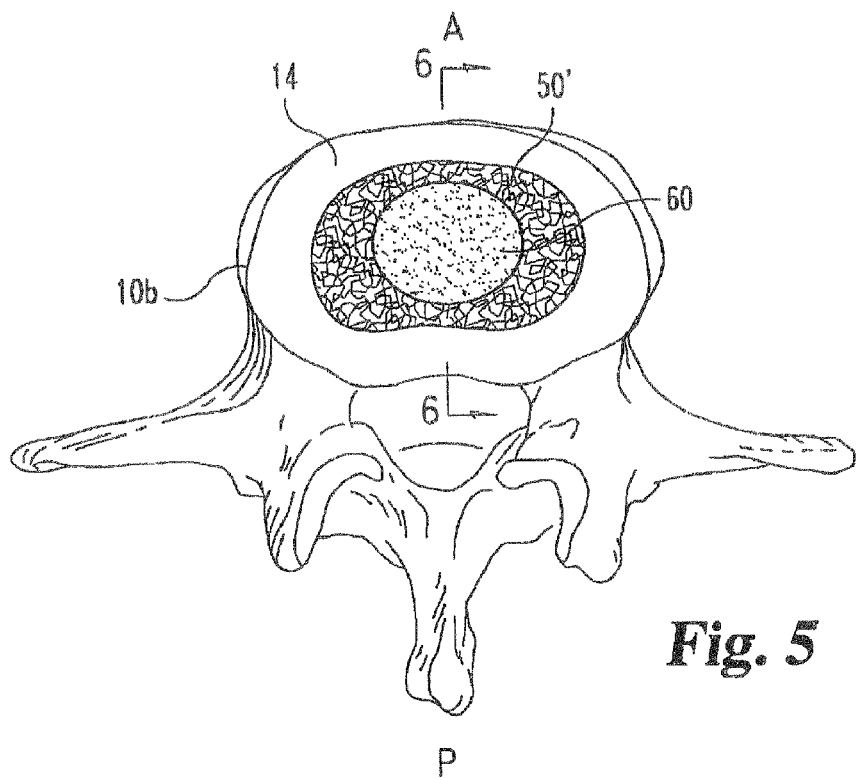
FIG. 5 is a diagrammatic illustration of the disc space of FIG. 4 with a second material in the disc space within the cured material.

Referring further to FIG. 4, enlargeable portion 34 is returned to its reduced size configuration so it can be removed from interbody device 50' and the disc space. This leaves a central cavity 52' surrounded by interbody device 50'. An endoscope 20 can be used to monitor distractor withdrawal and to check the integrity of interbody device 50'. Material delivery instrument 40 can then be repositioned, if necessary, in one of the access portals and used to deliver a second material 60 to central cavity 52' as shown in FIG. 5. Second material 60 can be artificial disc material, bioactive substance, rhBMP, autograft, or bioactive or osteoconductive carrier for bony fusion. In situations where second material 60 is fusion material, bony fusion can occur centrally while interbody device 50' provides stability of the disc space during fusion. It is further contemplated that in situations where fusion is desired, the endplates 11a, 11b could be reduced to bleeding bone via scraping, cutting, or reaming prior to placement of second material 60.

Figure 6:
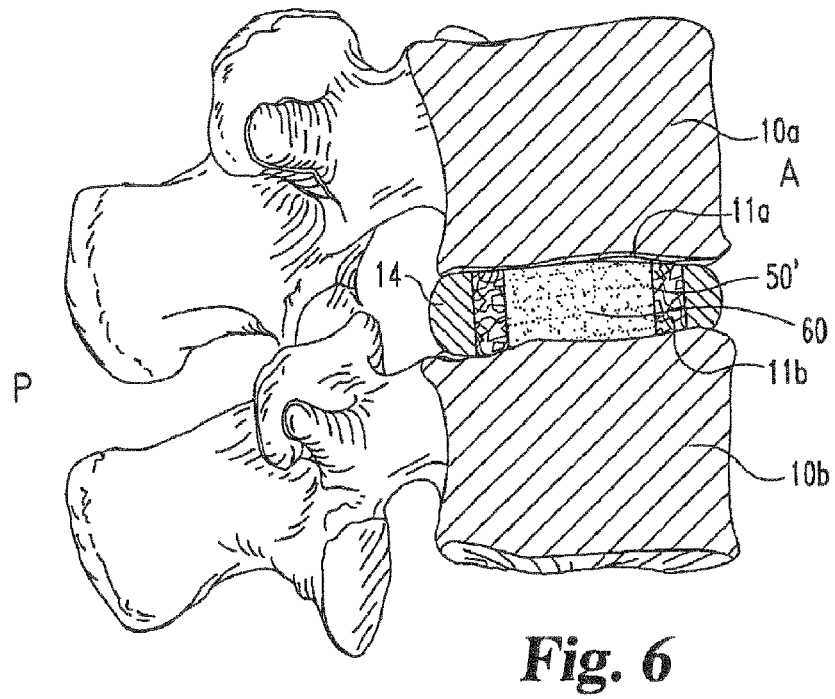
FIG. 6 is a diagrammatic illustration of in partial section through line 6-6 of FIG. 5.
Figure 7:
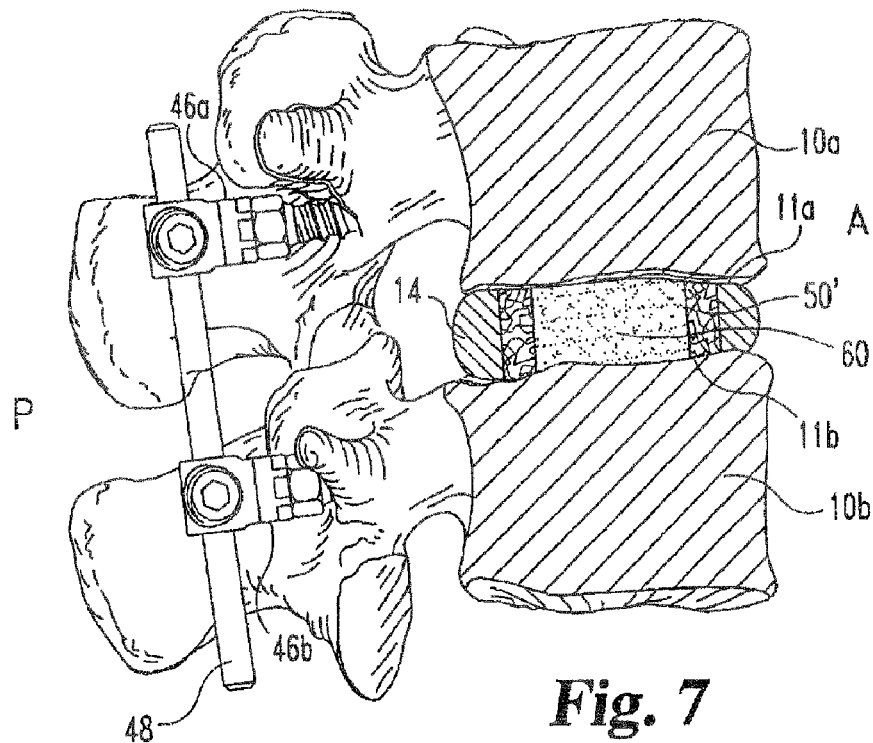
FIG. 7 is a diagrammatic illustration of the partial sectional view of FIG. 7 showing posterior stabilization instrumentation secured to the spinal column segment across the disc space.

Referring now to FIG. 6, there is shown a partial section view of the spinal column segment having interbody device 50' formed in a disc space as described above. Interbody device 50' conforms with the shape of endplates 11a, 11b and constrains second material 60 therein. In FIG. 7, there are shown posterior screws 46a, 46b secured to pedicles 16a, 16b and a rod 48 extending between and secured thereto. It is further contemplated that posterior stabilization could be provided with screws at the facet joints, or via a posterior plate secured to the vertebrae. Anterior or lateral stabilization plates secured to the vertebrae are also contemplated. Such supplemental fixation and stabilization devices are known in the art and will not be described further herein.

Figure 8:
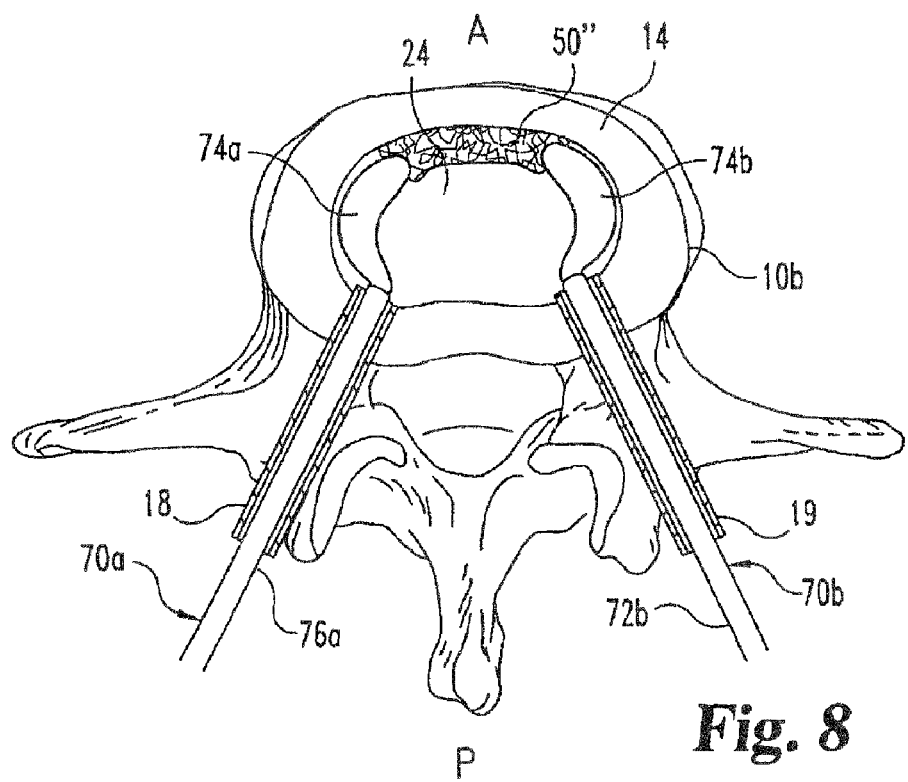
FIG. 8 is a diagrammatic illustration in the axial plane of a spinal disc space having a pair of distractors having enlargeable portions for bi-lateral distraction of the disc space.

Referring now to FIG. 8, there is shown another technique for forming an interbody device in a spinal disc space. The instruments used in the technique of FIG. 8 include a left side lateral distractor 70a and a right side lateral distractor 70b that is substantially identical to left side distractor 70a. Lateral distractors 70a, 70b each include shafts 72a, 72b and an enlargeable portion 74a, 74b, respectively, adjacent a distal end of the respective shaft. If enlargeable portions 74a, 74b were inflatable, shafts 72a, 72b would also define an inflation lumen. After completing procedures to form a prepared disc space as discussed above, lateral distractors 70a, 70b are positioned through bi-portal access ports 18, 19 and into the disc space 24. Enlargeable portions 74a, 74b each have a concavo-convex or banana-shaped configuration so that each can be positioned along the inner annulus wall and the apophyseal ring of the upper and lower vertebrae 10a, 10b while leaving the central portion of the disc space open. Further, the apophyseal ring in its most anterior portion between the distal tips of enlargeable portions 74a, 74b remains open for placement of and also remains open along its most posterior portion between the distal ends of enlargeable portions 74a, 74b. For example, as shown in FIG. 8, first material 50 has been placed in the anterior portion of the disc space by a material delivery instrument or catheter inserted through one of the access portals 18, 19 alongside the distractor to form a first interbody device segment 50" when cured. First material 50 could also be placed in the posterior portion to form a second interbody device segment (not shown). Additional interbody segments or pillars could be formed in the disc space, and second material 60 could then be placed or packed between the interbody segments.

Figure 9:
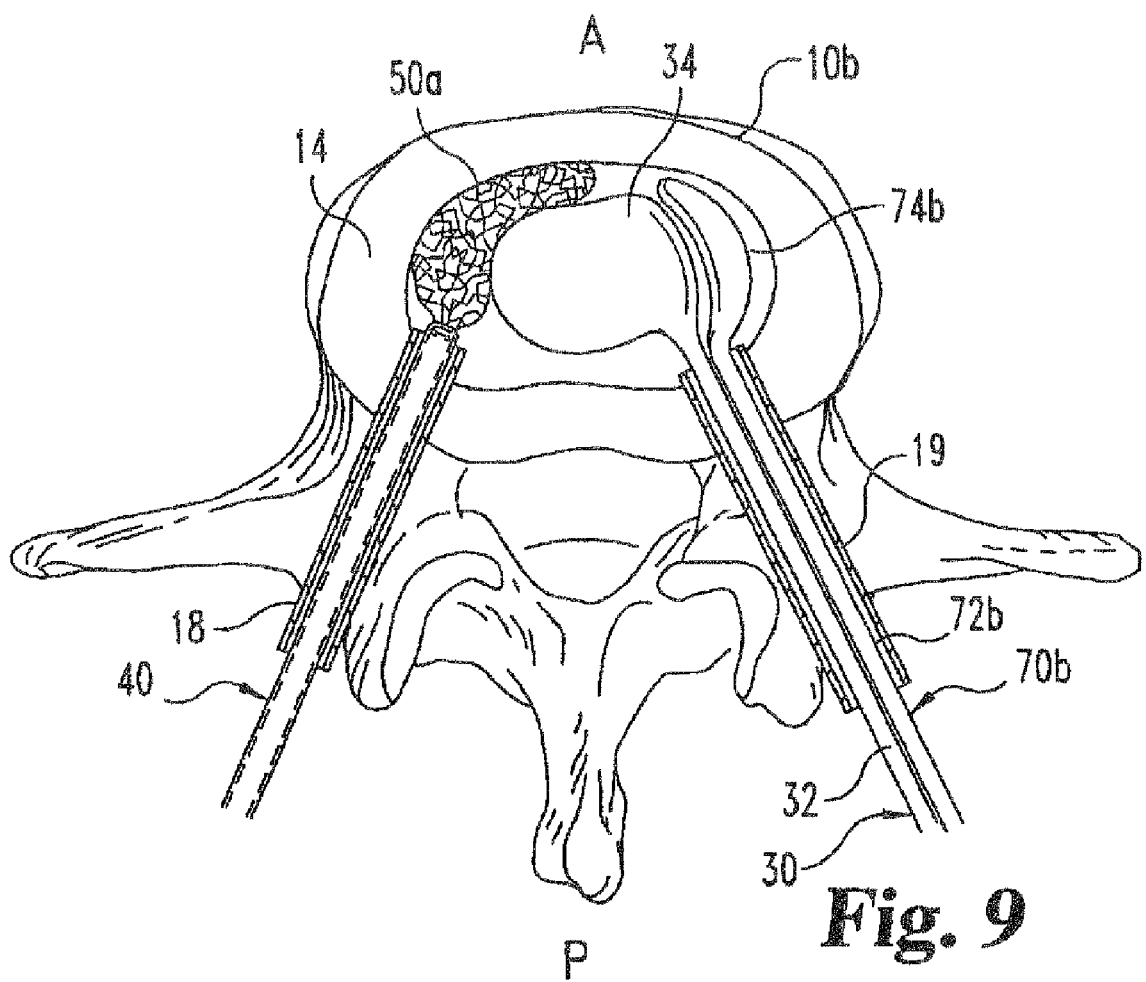
FIG. 9 is a diagrammatic illustration of a spinal disc space having another arrangement for dual distractors along with a first material positioned at a first lateral location in the disc space.

There are several distraction and material placement techniques afforded by use of lateral distractors as shown in FIG. 8. For example, after sequential bi-lateral distraction of the disc space, one of the lateral distractors could be reduced in size and withdrawn and this same side of the disc space could be provided with first material 50 from delivery instrument 40 to form a first lateral interbody device segment 50a as shown in FIG. 9. A single central distractor 30 can be used to block the central portion of the prepared disc space 24 while second lateral distractor 70b blocks the right lateral side of the disc space. Second lateral distractor 70b can then be withdrawn and additional first material 50 is provided to form a second interbody device segment (not shown) using enlargeable portion 34 as a form. After completion of the interbody device segments, second material 60 can be delivered into the space between the interbody device segments. Further, sequential distraction can be done in such a way that two lateral distractors 70a, 70b are left in prepared disc space 24 and second can be placed between the lateral distractors 70a, 70b. Second can then be used alone or in combination with one of the lateral distractors 70a, 70b as a form for placement of first material 50.

It is further contemplated that the placement location for first material 50 can be varied at any location about the apophyseal ring by using combinations of lateral distractors, anterior and posterior distractors, and central distractors. Further, it is contemplated first material 50 could be placed at multiple, discrete locations about the apophyseal ring to provide a number of columnar or segmented interbody devices in the disc space. These segmented interbody devices could be formed adjacent to and in contact with one another or formed with gaps therebetween. It is further contemplated that the positioning of the various interbody devices could be varied to accommodate the approach desired for material placement, including both uni-lateral injection or a bi-lateral placement.

In another embodiment, the banana-shaped lateral distractors 70a, 70b can be tapered in height to provide angulation between the vertebral endplates. For example, lordosis could be established by providing the enlargeable portions 74a, 74b with a greater height posteriorly than anteriorly. Further, the lateral distractors 70a, 70b can be provided with differing heights in order to distract one side of the disc space more than the other side, reducing or eliminating scoliosis. Alternatively, identical inflatable devices could be provided in which the inflatable portions have a height that corresponds to the internal inflation pressure supplied thereto. One of the lateral distractors could be inflated to a greater pressure than the contra-lateral side to provide differential distraction heights for each side. The same lateral distractor could be employed bi-laterally to change the lateral angulation of the disc space by varying the inflation pressure supplied to the enlargeable portion thereof.

After repairing scoliosis by providing the appropriate distraction and interbody devices, the disc space occupied by the enlargeable portions of the distractor is available for placement of bone growth material. For example, if two banana-shaped inflatable devices are used, a central cavity encompassed by the enlargeable portions remains after the portions are enlarged. Second material can then be placed in this central cavity. Additional first material can then be placed in the space previously occupied by the enlarged portions to provide structural peripheral support. Thus, this specific example contemplates initially central placement of a first material, such as bone growth material, and then the enlargeable distractors can be sequentially or simultaneously withdrawn from the disc space and a second material, such as a cement, placed around the central core of first material and against the enlargeable distractor portion, if any, remaining in the disc space to provide structural support of the disc space.

As discussed above, enlargeable portion 34 of the distractor 30 can be an inflatable device. In FIGS. 10-17, there are provided various embodiments of inflatable devices that can be used to perform disc space distraction. By providing inflatable devices of various shapes and sizes, different vertebral endplate contact areas can be formed thereby providing selection of the optimal inflatable device based on vertebral endplate load resistance, required distraction force, and the structural integrity of the pressurized inflated device. It should be understood, however, that the contact surface areas provided below are estimated based on a distraction height of 14 millimeters. The contact surface area of each balloon will vary depending on the degree to which the balloon is inflated. For distraction heights less than 14 millimeters, the contact are will be greater than 0.2 square inches. For distraction heights greater than 14 millimeters, the contact are will be less than 0.2 square inches. It should be further understood that the contact area for each balloon can be varied by changing the lateral and/or anterior-posterior dimensions of the balloon while retaining the same balloon shape.

Referring now to FIGS. 10a-10c, there is shown a first embodiment an inflatable device in the form of a balloon 100 having the shape of a center cylinder with frusto-conically tapered ends extending therefrom. Balloon 100 is in communication with an inflation lumen 102 and has upper vertebral endplate contacting surface 104 and opposite lower vertebral endplate contacting surface 106. As shown in FIG. 10b, surfaces 104, 106 have an oval shape with the rounded end portions of the oval positioned laterally of a longitudinal axis extending through inflation lumen 102 and balloon 100. Surfaces 104, 106 contact endplates 11a, 11b of the upper and lower vertebrae 10a, 10b, respectively, as shown in FIG. 10c. Balloon 100 has a central cylindrical portion 108 which defines contact surfaces 104, 106, and opposite frusto-conical portions 110, 112 distally and proximally extending therefrom, respectively, and tapered at an angle that avoids contact with the vertebral endplates. In one specific embodiment, it is estimated that balloon 100 has a contact surface area of about 0.2 square inches for each of the upper and lower contact surfaces 104, 106 when balloon 100 is expanded to distract the disc space to a height of 14 millimeters.

Referring now to FIGS. 11a-11c, there is shown another embodiment of an inflatable device in the form of a balloon 120 having a shape of a center cylinder with a pair of frusto-conically tapered ends extending from each end thereof. Balloon 120 is in communication with inflation lumen 122 and has upper vertebral endplate contacting surface 124 and opposite lower vertebral endplate contacting surface 126. As shown in FIG. 11b, surfaces 124, 126 have an oval shape with the rounded portions oriented distally and proximally along a longitudinal axis extending through inflation lumen 122 and balloon 120. Surfaces 124, 126 contact endplates 11a, 11b of the upper and lower vertebrae 10a, 10b, respectively, as shown in FIG. 11c. Balloon 120 has a central cylindrical portion 128 which defines a portion of contact surfaces 124, 126. Balloon 120 further includes first frusto-conical portions 130, 132 extending distally and proximally therefrom, respectively, which define the remaining portions of contact surfaces 124, 126. Frusto-conical portions 130, 132 are only tapered slightly and generally match the curvature of the vertebral endplates in order to provide additional contact area as compared to balloon 100. In one specific embodiment, balloon 120 has a contact surface area of about 0.3 square inches for each of the upper and lower contact surfaces 124, 126. Distal frusto-conical portion 134 and proximal frusto-conical portion 136 extend to the distal end of balloon 120 and to inflation lumen 122, respectively, and generally do not contact the vertebral endplates unless the balloon is sufficiently inflated to create such contact.

Referring to FIGS. 12a-12c, there is shown another embodiment an inflatable device in the form of a balloon 140 having a vertically oriented cylindrical shape. Balloon 140 is in communication with an inflation lumen 142 and has upper vertebral endplate contacting surface 144 and opposite lower vertebral endplate contacting surface 146. Surfaces 144, 146 contact endplates 11a, 11b of the upper and lower vertebrae 10a, 10b, respectively, as shown in FIG. 12c. Balloon 140 has a cylindrical body 148 which has circular upper and lower ends 150, 152 that define circular contact surfaces 144, 146 as shown in FIG. 12b. In one specific embodiment, balloon 140 has a contact surface area of about 0.5 square inches for each of the upper and lower contact surfaces 144, 146.

Referring now to FIGS. 13a-13c, there is shown another embodiment an inflatable device in the form of a balloon 160 having a horizontally oriented cylindrical shape. Balloon 160 in communication with an inflation lumen 162 and has a cylindrical body 168 with distal end 170 and opposite proximal end 172. Balloon 160 further includes upper vertebral endplate contacting surface 164 and opposite lower vertebral endplate contacting surface 166. As shown in FIG. 13b, contact surfaces 164, 166 have a substantially rectangular shape formed by the contact between the cylindrical sidewalls of cylindrical body 168 and endplates 11a, 11b of the upper and lower vertebrae 10a, 10b, respectively. In one specific embodiment, balloon 160 has a contact surface area of about 0.24 square inches for each of the upper and lower contact surfaces 164, 166.

Figure 14C:
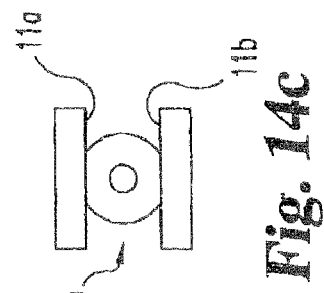
FIGS. 14*a*-14*c* show a side view, an end view and a plan view, respectively, of another embodiment inflatable distractor.
Figure 14B:
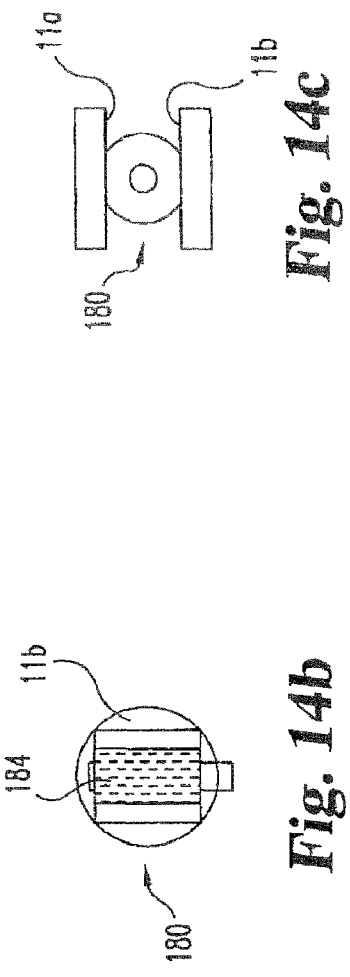
Figure 14A:
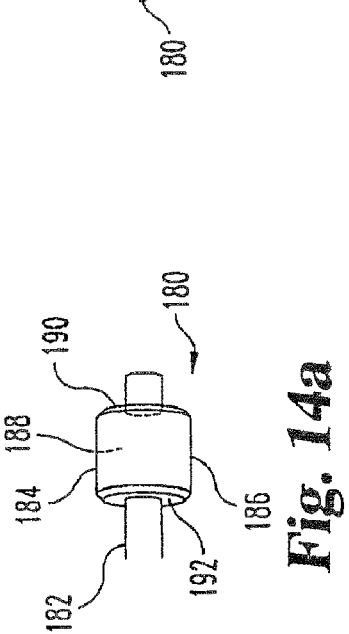

Referring to FIGS. 14a-14c, there is shown another embodiment an inflatable device in the form of a balloon 180 having a horizontally oriented cylindrical shape. Balloon 180 is in communication with inflation lumen 182 and has a cylindrical body 188 with distal end 190 and opposite proximal end 192. Balloon 180 further includes upper vertebral endplate contacting surface 184 and opposite lower vertebral endplate contacting surface 186. As shown in FIG. 14b, contact surfaces 184, 186 have a rectangular shape formed by the contact between the cylindrical sidewalls of cylindrical body 188 and endplates 11a, 11b of the upper and lower vertebrae 10a, 10b, respectively. In one specific embodiment, balloon 180 has a contact surface area of about 0.3 square inches for each of the upper and lower contact surfaces 184, 186. Balloon 180 is similar in shape to balloon 160, but has a shorter length between its distal and proximal ends to allow balloon 180 to extend further laterally in the disc space than balloon 160 and thus increasing the vertebral endplate contact area.

Figure 15C:
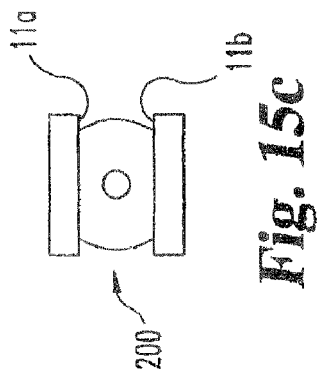
FIGS. 15*a*-15*c* show a side view, an end view and a plan view, respectively, of another embodiment inflatable distractor.
Figure 15B:
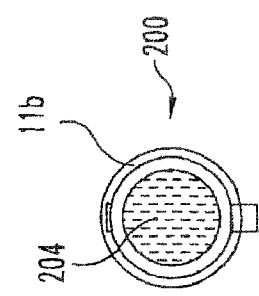
Figure 15A:
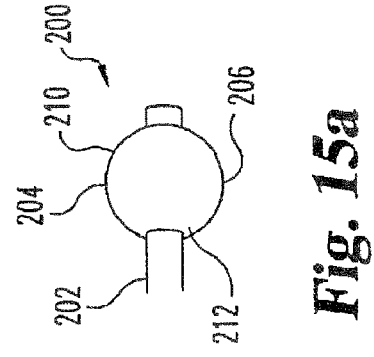

Referring to FIGS. 15a-15c, there is shown another embodiment an inflatable device in the form of a balloon 200 having a spherical shape. Balloon 200 is in communication with an inflation lumen 202 and has upper vertebral endplate contacting surface 204 and opposite lower vertebral endplate contacting surface 206. Surfaces 204, 206 are formed on spherical body 208 and have a circular shape in contact with endplates 11a, 11b of the upper and lower vertebrae 10a, 10b, respectively. Spherical body 208 has opposite distal and proximal ends 210, 212 respectively. In one specific embodiment, balloon 200 has a diameter of 22 millimeters which provides a contact surface area of about 0.35 square inches for each of the upper and lower contact surfaces 204, 206.

In FIGS. 16a-16c there is shown another embodiment spherically shaped balloon 220 having a spherical body 228 in communication with inflation lumen 222. Spherical body 228 includes contact surfaces 224, 226 forming a circular contact surface with endplates 11a, 11b. In this embodiment, balloon 220 has a diameter of 24 millimeters and the endplate contact surface areas of surfaces 224, 226 are each 0.45 square inches.

Referring now to FIG. 17, there is shown an inflatable device having a pear shaped balloon 240 in fluid communication with an inflation shaft 242. Balloon 240 includes upper surface 244 and an opposite lower surface 246. Upper surface 244 has first vertebral endplate contacting node 244a, a second vertebral endplate contacting node 244b and a concave portion 244c extending therebetween. Similarly, lower surface 246 has first vertebral endplate contacting node 246a, a second vertebral endplate contacting node 246b and a concave portion 246c extending therebetween. Balloon 240 is shaped such that the contacting nodes are positionable at the apophyseal ring and the concave surfaces span weaker bony material at the central portion of the vertebral endplate. It is further contemplated that such a shape could be provided to establish lordosis by, for example, providing the anteriorly positioned node with a height less than the posteriorly oriented node.

In addition to the above-described shapes, other shapes for the enlargeable portion 34 of distractor 30 are also contemplated. For example, the enlargeable portion can have a shape that corresponds to the shape of the vertebral endplates, such as a kidney bean shape, or can have a square or rectangular cuboid shape. It is also desirable that first does not adhere to the enlargeable portion 34 while it is curing. Thus, various coatings can be applied to the exterior surface of enlargeable portion 34 such as, for example, Teflon spray or silicone oil. Other coatings are also contemplated, so long as they prevent the adhesion of first material 50 and enlargeable portion 34. For embodiments in which enlargeable portion 34 is an inflatable device, the device should also be made from a tough yet elastic material that can withstand the inflation pressures applied thereto while also retaining the capability to return to a reduced size configuration for insertion and withdrawal from the disc space and through the access port.

The inflatable devices of the present invention can be designed to accommodate the patient anatomy. One factor considered in such a design is the force required to distract the disc space to the desired disc space height. The ability of the vertebral endplates to resist contact pressure has been found to decrease with patient age. For example, one study found those persons in the range of 20-30 years have a vertebral endplate resistance capability of 1500 pounds per square inch, those persons in the range of 40-60 year olds have a vertebral endplate resistance capability of 1050 pounds per square inch, and those persons over 60 year olds have a vertebral endplate resistance capability of 594 pounds per square inch. In order to distract the disc space with an inflatable device, sufficient pressure must be exerted to overcome the tension from the muscles and ligaments that have become accustomed to the collapsed condition of the disc space. However, the pressure on the vertebral endplates must remain within acceptable limits.

Based on the contact area of the balloon, the load the balloon will exert on the vertebral endplates to distract the disc space can be determined. The pressure exerted on the vertebral endplates can also be determined and the balloon sized so that the contact pressure does not exceed the vertebral endplate resistance capability of the patient. The following table presents the maximum allowable load for various balloon contact areas based on the vertebral endplate resistance for the patient ranges provided above:

| | Maximum Allowable Endplate Load | | |
|---|---|---|---|
| Contact Area | 20-30 yr olds | 40-60 yr olds | 60+ yr olds |
| 0.5 sq. in. | 750 lbs | 525 lbs | 297 lbs |
| 0.4 sq. in | 600 lbs | 420 lbs | 238 lbs |
| 0.3 sq. in. | 450 lbs | 315 lbs | 178 lbs |
| 0.2 sq. in. | 300 lbs | 210 lbs | 119 lbs |
| 0.1 sq. in. | 150 lbs | 105 lbs | 59 lbs |

Figure 18:
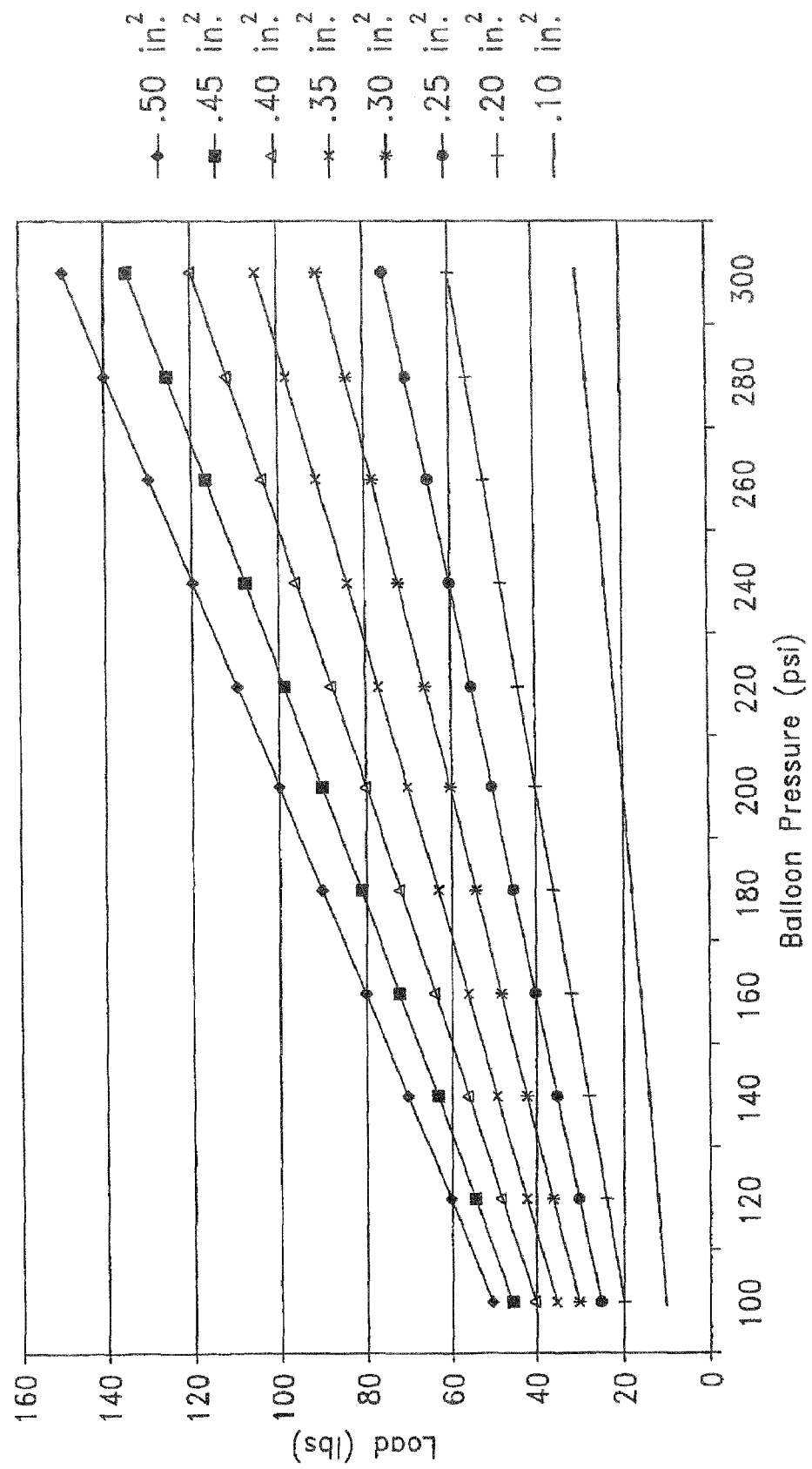
FIG. 18 is a graphical representation of the load applied to the vertebral endplates versus inflation pressure for inflatable distractors having various vertebral endplate contact areas.

As shown in FIG. 18, a graphical representation is provided to represent the relationship between the balloon pressure and the load exerted by the balloon for various sizes of contact areas for the balloons ranging between 0.1 square inches to 0.5 square inches. From this information, a balloon contact area size and pressure can selected that is within the maximum allowable load for a particular patient. For example, if 100 pounds is required to distract the vertebrae to the desired height, then a balloon having contact surface areas of 0.5 square inches would apply a vertebral endplate load of about 100 pounds at an inflation pressure of 200 psi. The distraction load of 100 pounds for the 0.5 square inch contact area is well below the maximum allowable endplate load for each of the patient age ranges provided above.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A spinal surgical instrument for distracting a disc space, comprising:
   a shaft extending between a proximal end and a distal end, said shaft having an inflation lumen and a material delivery lumen; and
   a pear shaped inflatable portion adjacent said distal end, said inflatable portion having an interior in communication with said inflation lumen and a reduced size configuration for insertion into the disc space and an enlarged inflated configuration, wherein when in said inflated configuration said inflatable portion defines an upper vertebral endplate contacting surface and an opposite lower vertebral endplate contacting surface, each of said upper and lower vertebral endplate contacting surfaces having a vertebral endplate contacting area, wherein in said inflated configuration each of said vertebral endplate contacting surfaces of said inflatable portion has an anterior contacting node and a posterior contacting node and a concave surface extending between said anterior and posterior contacting nodes so that said anterior and posterior contacting nodes are positionable against apophyseal rings of vertebral endplates adjacent the disc space and the concave surfaces span central portions of the vertebral endplates between the anterior and posterior contacting nodes, wherein a height of said anterior contacting node is less than a height of said posterior contacting node,
   wherein said material delivery lumen extends through said inflatable portion and opens at said distal end of said shaft,
   wherein said delivery lumen delivers a material in a first condition about said inflatable portion when said inflatable portion is in said inflated configuration in the disc space, said material being changeable to a second condition after delivery.

2. The instrument of claim 1, wherein when in said inflated configuration said inflatable portion is sized to occupy the disc space with a void formed between the inflatable portion and an inner wall of an annulus surrounding the disc space annulus.

3. The instrument of claim 1, wherein said material comprises a bone cement, said bone cement being flowable in said first condition and curable to obtain a solid body between the vertebral endplates adjacent the disc space in said second condition.

4. The instrument of claim 1, wherein when said inflatable portion is in said enlarged inflated configuration said vertebral endplate contacting area of each of said upper and lower vertebral endplate contacting surfaces is in the range of 0.1 square inches to 0.5 square inches.

5. The device of claim 1 wherein said inflatable portion further comprises a non-adherence coating on at least a portion of an exterior surface of said inflatable portion.

6. The device of claim 5 wherein said non-adherence coating is selected from the group consisting of Teflon spray and silicone oil.

7. A spinal surgical device implantable in a disc space, comprising:
   a shaft extending between a proximal end and a distal end, said shaft having an inflation lumen and a material delivery lumen; and
   a pear shaped inflatable portion adjacent said distal end, said inflatable portion having an interior in communication with said inflation lumen and a reduced size configuration for insertion into the disc space and an enlarged inflated configuration, wherein when in said inflated configuration said inflatable portion is sized to contact vertebral endplates adjacent the disc space and restore the disc space to a desired disc space height, said inflatable portion is further sized and shaped to occupy the disc space with a void formed between the inflatable portion and an inner wall of an annulus surrounding the disc space annulus, wherein in said inflated configuration said inflatable portion includes opposite vertebral endplate contacting surfaces and each of said vertebral endplate contacting surfaces has an anterior contacting node and a posterior contacting node with a concave surface extending between said anterior and posterior contacting nodes so that said anterior and posterior contacting nodes are positionable against apophyseal rings of the vertebral endplates adjacent the disc space and the concave surfaces span central portions of the vertebral endplates between the anterior and posterior contacting nodes, wherein a height of said anterior contacting node is less than a height of said posterior contacting node; and
   a first material in the void, wherein said material delivery lumen extends through said inflatable portion and opens at said distal end of said shaft, wherein said delivery lumen delivers the first material in a first condition about said inflatable portion when said inflatable portion is in said inflated configuration in the disc space, said first material being changeable to a second condition after delivery.

8. The device of claim 7, wherein when inflated each of said upper and lower vertebral endplate contacting surfaces have a vertebral endplate contacting area in the range of 0.1 square inches to 0.5 square inches.

9. The device of claim 7, wherein said first material comprises a bone cement, said bone cement being flowable in said first condition and curable to obtain a solid body between the endplates adjacent the disc space in said second condition.

10. The device of claim 9 wherein said inflatable portion further comprises a non-adherence coating on at least a portion of an exterior surface of said inflatable portion.

11. The device of claim 10 wherein said non-adherence coating is selected from the group consisting of Teflon spray and silicone oil.

* * * * *